(12) United States Patent
Lyons et al.

(10) Patent No.: US 6,667,156 B2
(45) Date of Patent: *Dec. 23, 2003

(54) DIAGNOSIS AND TREATMENT OF NEUROECTODERMAL TUMORS

(75) Inventors: Susan A. Lyons, Birmingham, AL (US); Harald W. Sontheimer, Birmingham, AL (US)

(73) Assignee: UAB Research Foundation, Birmingham, AL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/296,031

(22) Filed: Apr. 21, 1999

(65) Prior Publication Data

US 2002/0146749 A1 Oct. 10, 2002

Related U.S. Application Data

(63) Continuation-in-part of application No. 08/774,154, filed on Dec. 26, 1996, now Pat. No. 5,905,027.
(60) Provisional application No. 60/009,283, filed on Dec. 27, 1995.

(51) Int. Cl.[7] ...................... G01N 33/574; G01N 33/53; G01N 33/48
(52) U.S. Cl. .................. 435/7.23; 435/7.1; 436/63; 436/64; 436/813
(58) Field of Search ............................. 435/7.23, 7.1; 436/63, 64, 813

(56) References Cited

U.S. PATENT DOCUMENTS

| | | | |
|---|---|---|---|
| 5,212,290 A | 5/1993 | Vogelstein et al. | 530/387.7 |
| 5,223,253 A | 6/1993 | Hall et al. | 424/88 |
| 5,626,862 A | 5/1997 | Brem et al. | 424/426 |
| 5,750,376 A | 5/1998 | Weiss et al. | 435/69.52 |
| 5,756,340 A | 5/1998 | Hammock et al. | 435/234 |
| 5,905,027 A * | 5/1999 | Ullrich et al. | 435/7.23 |
| 6,028,174 A | 2/2000 | Ullrich et al. | 530/350 |

FOREIGN PATENT DOCUMENTS

WO  WO 97/24619  * 7/1997

OTHER PUBLICATIONS

Soroceanu et al., Use of Chlorotoxin for Targeting of Primary Brain Tumors, 1998, Cancer Research 58: 4871–4879.*
Baker, (1991) Effects of an epithelial Cl⁻ channel blocker on whole cell voltage clamp and patch clamp recordings from a human astrocytoma in culture, J. Physiol. 438:128–129.
Brismar et al., (1989) Inward rectifying potassium channels in human malignant glioma cells, Brain Res. 480:249–258.
Brismar et al., (1989) Potassium and sodium channels in human malignant glioma cells, Brain Res. 480:259–267.
Chiu et al., (1989) The role of potassium channels in Schwann cell proliferation in Wallerian degeneration of explant rabbit sciatic nerves, J. Physiol. 408:199–222.
Deane et al., (1992) An alternative pathway of B cell activation: stilbene disulfonates interact with a Cl⁻binding motif on AEn–related proteins to stimulate motogenesis, Eur. J. Immunol. 22:1165–1171.
DeBin et al., (1991) Chloride channel inhibition by the venom of the scorpion *Leiurus quinquestriatus*, Toxicon. 29:1403–1408.
DeBin et al., (1993) Purification and characterization of chlorotoxin, a chloride channel ligand from the venom of the scorpion, Am. J. Physiol. 264:C361–369.
DeMuralt et al., (1983) Reactivity of antiglioma monoclonal antibodies for a large panel of cultured gliomas and other neuroectoderm derived tumors, Anticancer Res. 3:1–6.
Goldstein et al., (1986) The Blood Brain Barrier, Sci. Am. 255:74–83.
Gray et al., (1986) A voltage–gated chloride conductance in rat cultured astrocytes, Proc. R. Soc. Lond. 228:267–288.
Grissmer et al., (1993) Calcium–activated potassium channels in resting and activated human T lymphocytes, J. Gen. Phys. 102:601–630.
Hosli et al. (1990) Evidence for GABA–B receptors on cultured astrocytes of rat CNS: autoradiographic binding studies, Exp. Brain. Res. 80:621–625.
Huang et al. (1994) Potassium channel induction by the Ras/Raf signal transduction cascade, J. Biol. Chem. 269:31183–31189.
Jalonen, (1993) Single–channel characteristics of the large–conductance anion channel in rat cortical astrocytes in primary culture, Glia 9:227–237.
Kunwar et al., (1993) Cytotoxicity and antitumor effects of growth factor–toxin fusion proteins on human glioblastoma multiforme cells, J. Neurosurg. 79:569–576.
Nilius et al. (1992) Potassium channels and regulation of proliferation of human melanoma cells, J. Physiol. 445:537–548.

(List continued on next page.)

Primary Examiner—Shin-Lin Chen
(74) Attorney, Agent, or Firm—Morgan, Lewis & Bockius LLP

(57) ABSTRACT

The present invention provides fusion proteins for the detection and treatment of neuroectodermal tumors. Previous work demonstrated that chlorotoxin is specific for glial-derived or meningioma-derived tumor cells. The current invention has extended the use of chlorotoxin-cytotoxin fusion proteins to treat the whole class neuroectodermal tumors such as gliomas, meningiomas, ependymonas, medulloblastomas, neuroblastomas, gangliomas, pheochromocytomas, melanomas, PPNET's, small cell carcinoma of the lung, Ewing's sarcoma, and metastatic tumors in the brain. Also, diagnostic methods are provided for screening neoplastic neuroectodermal tumors.

18 Claims, 15 Drawing Sheets

OTHER PUBLICATIONS

Pappas et al. (1994) Reduction of glial proliferation by K$^+$channel blockers is mediated by changes in pH$_i$, NeuroReport 6:193–196.

Pappone et al.,(1993) Blockers of voltage–gated K channels inhibit proliferation of cultured brown fat cells, Am. J. Physiol. 264:C1014–1019.

Phillips et al., (1994) Transforming growth factor–alpha–pseudomonas exotoxin fusion protein (TGF–α–PE38) treatment of subcutaneous and intracranial human glioma and medulloblastoma xenografts in athymic mice, Cancer Research 54:1008–1015.

Puro et al., (1989) Retinal glial cell proliferation and ion channels: A possible link, Invest. Ophthalmol. Vis. Sci. 30:521–529.

Sakamoto et al., (1996) Identification of a new outwardly rectifying Cl$^-$channel that belongs to a subfamily of the ClC Cl$^-$channels, J. Biol. Chem. 271:10210–10216.

Somogyi et al., (1989) Subcellular localization of benzodiazepine/GABA$_A$ receptors in the cerebellum of rat, cat and monkey using monoclonal antibodies, J. Neurosci. 9:2197–2209.

Sontheimer, (1994) Voltage–dependent ion channels in glial cells, Glia 11:156–172.

Steinmeyer et al., (1995) Cloning and functional expression of rat CLC–5, a chloride channel related to kidney disease, J. Biol. Chem. 270:31172–31177.

Uchida et al., (1995) Localization and functional characterization of rat kidney–specific chloride channel ClC–K1, J. Clin. Invest. 95:104–113.

Ullrich et al., (1996) Human astrocytoma cells express a unique chloride current, NeuroReport 7:1020–1024.

Ullrich et al., (1996) Biophysical and pharmacological characterization of chloride currents in human astrocytoma cells, Am. J. Physiol. 270:C1511–1521.

Wilson et al., (1993) Mitogenic factors regulate ion channels in Schwann cells cultured from newborn rat sciatic nerve, J. Physiol. 470:501–520.

Woodfork et al., (1995) Inhibition of ATP–sensitive potassium channels causes reversible cell–cycle arrest of human breast cancer cells in tissue culture, J. Cell. Physiol. 162:163–171.

* cited by examiner

Normal Brain

Pheochromocytoma

TM-601  Control  H&E stain

Melanoma to Brain

TM-601　　　　　Control　　　　H&E stain

Normal Breast Skin

TM-601      Control      H&E stain

DIAGNOSIS AND TREATMENT OF NEUROECTODERMAL TUMORS

This application is a continuation-in-part of U.S. application Ser. No. 08/774,154 filed Dec. 26, 1996) now U.S. Pat. No. 5,905,027 which claims the benefit of U.S. Provisional Application No. 60/009,283 (filed Dec. 27, 1995).

FEDERAL FUNDING LEGEND

This invention was produced in part using funds from the Federal government under NIH grant no. R01 NS 36692. Accordingly, the Federal government has certain rights in this invention.

BACKGROUND OF THE INVENTION

1. Field of the Invention

The present invention relates generally to the fields of cell physiology, neurology, developmental biology, and oncology. More specifically, the present invention relates to novel methods of using a chlorotoxin sensitive cytoplasmic protein for the diagnosis and treatment of primitive neuroectodermal tumors (PNET).

2. Description of the Related Art

During embryonic development, the future nervous system forms from a specialized layer of ectodermal cells called the neuroectoderm. This layer extends longitudinally along the body axis congruent with the future spinal column. Invagination of the neuroectoderm gives rise to the neural tube from which essentially all central nervous system (CNS) components including the spinal cord develop. Specialized cell clusters along the rim of the invaginating neural tube stay separate from the tube and from the neural crest. These highly migratory neuroectodermal cells give rise to specialized cells throughout the body including Schwann cells, neuronal cells of the peripheral nervous system (PNS) (enteric, parasympathetic, sympathoadrenal, and sensory neurons), pigment cells (melanocytes), endocrine cells and cells forming connective tissue of the face and neck. Since these cells share a common embryonic origin with central nervous system cells, it is not surprising that these cells, or the tumors developing from these cells, share some genetic and antigenic phenotypes with central nervous system cells.

For example, melanomas and glioblastomas share a common mutation in the gene encoding for the epidermal growth factor receptor (EGFR) (1). Malignant astrocytomas and neurofibromas not only express high levels of the epidermal growth factor receptors but also vascular endothelial growth factor receptor (VEGF-R) and platelet-derived growth factor receptor (PDGF-R) (2). A high expression of the mutant variant, EGFRvIII, has been demonstrated in glial tumors as well as the extracellular matrix proteins, GP 240 and tenascin (3). Tenascin and the ganglioside-3',6'-isoLD1 have been found in both gliomas and primitive neuroectodermal tumor tissues (3). In another study, antibodies to tenascin bound extensively to CNS gliomas and also to melanomas, breast, lung and squamous cell carcinomas (4). Another ganglioside, GD2, has been shown to be a common antigen marker in both gliomas and primitive neuroectodermal tumor tissues (5). Other common antigens between melanomas and gliomas were demonstrated by showing that Tyr, TRP-1, TRP-2 and gp100 gene products are commonly found in both melanoma and glioma tumors (6). Common cytokines or their receptors linking tumors of astrocytomas, ependymomas and primitive neuroectodermal tumors have been identified as: interleukin (IL) IL-1 alpha, IL-1, IL-1R1, IL-1R antagonist and transforming growth factor (TGF) TGF-beta 1 (11).

Another class of proteins used as markers for gliomas and primitive neuroectodermal tumors are the cytoskeletal proteins, neurofilament (NF), glial fibrillary acidic protein (GFAP), intermediate filaments (IF), intermediate associated protein filament (IFAP), vimentin, nestin and keratins. These markers have been used to determine stages of differentiation along the various cell lineages (12). New evidence linking astrocytomas with certain primitive neuroectodermal tumor tumors is the cytoskeleton marker of IFAP-300 kDa, a marker of immature glia (13).

Further arguments for a tight linkage of neuroectodermally derived cells in the central nervous system and periphery can be made based on their similar dependence on epigenetic influences. For example, sympathoadrenal precursor neurons require basic fibroblast growth factor (bFGF) to proliferate and differentiate, but survival of these cells depends on nerve growth factor (NGF) responsiveness and nerve growth factor availability (14). A similar scenario is required for each of the other cell types. Not only are growth and trophic factors necessary but cytokines and hormones are needed for which links remain to be elucidated between primitive neuroectodermal tumors and gliomas.

However, despite this list of similarities shared between neuroectodermally derived cells, these cells are distinct entities with unique cytological, biochemical and functional features. Indeed, the list of unique features not shared with other neuroectodermally derived cells by far exceeds the above mentioned shared phenotypes. Thus, one can not assume a priori that expression of a certain antigen or phenotype is to be expected in a given cell type based on expression by any other member of the neuroectodermally derived cell types.

Neuroblastomas generally express a selective increase in the gene copy number of the MYCN gene found in fetal stages of brain development suggesting links between the origin of the cells and the ability of neoplastic cells to dedifferentiate (7). However, this gene has yet to be demonstrated in the glioma cells. Other proteins that are not common to both glioma and primitive neuroectodermal tumors have been demonstrated. CD99 immunoreactivity is used as a tool in identifying primitive neuroectodermal tumors (8) and has been shown in Ewing's sarcoma tumors although not in gliomas (9). Another factor, stem cell factor and its receptor, c-kit, are also expressed in both primitive neuroectodermal tumor and Ewing's Sarcoma tumors (10).

The common origin and ability to respond to internal and external signals during the normal developmental processes suggests that central nervous system cells and peripheral neuroectodermally derived cells may also share common mechanisms during pathological developments as for example, during neoplasia. Such neoplastic tissues include CNS gliomas that are glial-derived tumor cells specific to the CNS. They metastasize only within the CNS including the spinal column. They are believed to originate from at least three separate lineages either from undifferentiated precursor cells or by dedifferentiation of astrocytes, oligodendrocytes or ependymal cells.

Primitive neuroectodermal tumors (PNET) are found both in the CNS and PNS. Primitive neuroectodermal tumors found only in the PNS are referred to as peripheral primitive neuroectodermal tumors (PPNET). Primitive neuroectodermal tumors manifest preferentially in children and have capacity for developing into a variety of neuronal, astrocytic, ependymal, muscular and melanotic lines. The conceptual basis of grouping these tumors together is based upon sharing common progenitor cells as well as sharing similar neoplastic transformations leading to tumors of similar morphological features and biological behavior. However, there remains controversy in placing all primitive neuroectodermal tumors into the same categories. The following paragraphs demonstrate examples of the overlap of common antigens between the various types of CNS and PNS tumors.

Supratentorial primitive neuroectodermal tumors include cerebral medulloblastomas, cerebral neuroblastomas, 'blue' tumors, ependymoblastoma and other primitive neuroectodermal tumors, such as pineoblastomas (WHO grade IV). The most useful markers for these tumors include GFAP, NFP, desmin and melanin. Others antigens found in these tumors are vimentin, nestin, keratin but are not useful for diagnostic purposes.

Peripheral neuroblastic tumors of the adrenal gland (medulla) and sympathetic nervous system are the most common type of childhood tumor outside of the CNS. Primary sites for these primitive neuroectodermal tumors are in the adrenals, abdominal, thoracic, cervical and pelvic sympathetic ganglia but include other primary sites as orbit, kidney, lung, skin, ovary, spermatic cord, and urinary bladder. Specific names of these related tumors are pheochromocytomas, paraganglioma, neuroblastomas, ganglioneuromas, ganglioneuroblastomas, neurofibromas, schwannomas, and malignant peripheral nerve sheath tumors. These all share common origin in the neural crest. Neuroblastomas all share high TRK-A (NGFR) and CD44 expressions. Neuronal specific enolase (NSE), synaptophysin, neural filament (NF) protein, GD2, tyrosine hydroxylase (TH) and chromogranin are used as diagnostic markers also found in medulloblastomas. Neuroblastomas generally express a selective increase in the gene copy number of the MYCN gene found in fetal stages of brain development (7).

Medulloblastomas are members of the primitive neuroectodermal tumors that are described as highly malignant embryonal tumors of the CNS found in the cerebellum (WHO grade IV). A common antigen of these medulloblastoma and other neuronal lineage tumors is synaptophysin (not found in glial or mesenchymal brain tumors). Nestin (IF protein) is found in developing CNS precursor cells and in medulloblastomas and in some peripheral neuroectodermal origin cells. Nestin (and vimentin) are found in medulloblastomas, astrocytomas, glioblastomas, ependymomas, gangliogliomas and meningiomas (only GFAP is found in the astrocytic-derived cells, which are occasionally 'trapped' in medulloblastomas). Increased levels of neural-cellular adhesion molecule (N-CAM) found in these tumors, may reflect levels of differentiation in the development of tumors (15). While varying levels of nerve growth factor (NGF), are found in nearly all tumors, medulloblastomas exhibited substantial reactivity to the NGF receptor and related proteins, neurotrophin (NT) NT-3, TRK-C and brain derived neurotrophic factor (BDNF) (16).

Melanomas, arising from melanocytes follow a graded development from diffuse melanocytosis, to melanocytoma to malignant melanomas. S100 protein is a marker for these tumors, as vimentin and NSE reactivity are variable.

Small cell neuroendocrine carcinomas of the lung are highly invasive and typically found in adult smokers. They have been shown to exhibit reactivity to many of the neural and neuroendocrine markers (some of them similar to N-CAMs) for tumor differentiation as peripheral primitive neuroectodermal tumors, gliomas, and ependymomas. These markers include neural specific enolase and extremely high c-src expression (17).

A feature conspicuously shared between developing CNS cells and neural crest derived cells is their propensity to migrate either towards a target or target area. It is believed that this ability is lost after cell differentiation and maturation. However, tumors of the CNS show significant cell migration and invasion into healthy brain, suggesting that cell have maintained or regained this enhanced migratory ability. It is, thus, not surprising that neoplastic transformation of neuroectodermally derived cells outside the CNS would have similar migratory abilities. At the intended destination, these cells differentiate into their final phenotype, similar to normal development, influenced by several trophic factors crucial for the proliferation and differentiation of various cell types.

The prior art is deficient in the lack of an diagnostic and therapeutic agents specifically targeted to primitive neuroectodermal tumors. The present invention fulfills this long-standing need and desire in the art.

SUMMARY OF THE INVENTION

In one embodiment of the current invention, a method is described for the treatment of tumors of neuroectodermal origin by administering a ligand specific for this class of tumors fused to a cytotoxic moiety. Specific neuroectodermal tumor tumors which can be treated in this manner include gliomas, meningiomas, ependymomas, medulloblastomas, neuroblastomas, gangliomas, pheochromocytomas, melanomas, peripheral primitive neuroectodermal tumors, small cell carcinoma of the lung, Ewing's sarcoma, and metastatic tumors of neuroectodermal origin in the brain.

In the preferred embodiment, the neuroectodermal tumor specific ligand is chlorotoxin in the form of a fusion protein of chlorotoxin with cytotoxic moiety. The chlorotoxin may be native, synthetic or recombinant chlorotoxin. Possible cytotoxic moieties include gelonin, ricin, saponin, pseudonomas exotoxin, pokeweed antiviral protein, diphtheria toxin, and complement proteins.

In another embodiment of the current invention, the neuroectodermal tumor specific ligand is an antibody against the chlorotoxin receptor, presumably a 72 kDa chloride channel. The antibody may be fused to gelonin, ricin, saponin, pseudonomas exotoxin, pokeweed antiviral protein, diphtheria toxin, and complement proteins.

In yet another embodiment of the current invention, a method of differentiating neuroectodermal tumor-derived neoplastic tumor tissue from non-neoplastic tissue is presented. This is accomplished by exposing the tissue with labeled chlorotoxin and measuring the binding of the labeled chlorotoxin. An elevated level of binding relative to normal tissue is indicative that the tissue is neoplastic. In one embodiment, the label is a fluorescent moiety which is detected by fluorescent microscopy, fluorescent activated cell sorting or a fluorescent plate reader. Alternatively, the chlorotoxin may be radiolabeled (eg. $^{131}$I-chlorotoxin or $^{125}$I-chlorotoxin; a person having ordinary skill in this art would readily recognize other useful radiolabels) and detected by positron emission tomography scanning. Alternatively, the chlorotoxin may be conjugated to a non-fluorescent detection moiety such as biotin and detected immunohistochemically or by use of a calorimetric assay.

BRIEF DESCRIPTION OF THE DRAWINGS

So that the matter in which the above-recited features, advantages and-objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
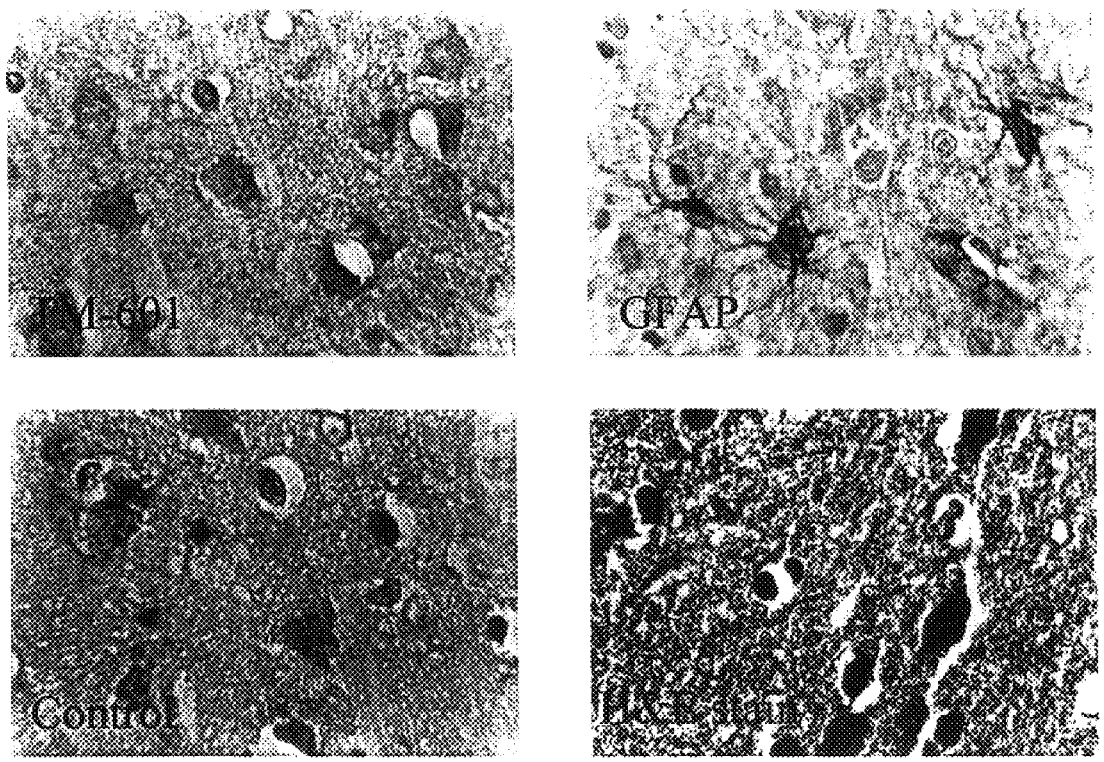
FIG. 1 shows the positive immunohistochemical staining of a glioblastoma multiform (GBM) tumor with chlorotoxin. The brown reaction product of DAB 3'3'-diaminobenzidine with biotinylated chlorotoxin is clearly visible in the TM-601 stained section. TM-601: biotinylated chlorotoxin stained, counter-stained with methyl green; Control: methyl green only; and, H&E stain: hematoxylin and eosin.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

As used herein, the term "cDNA" shall refer to the DNA copy of the mRNA transcript of a gene.

As used herein, the term "derived amino acid sequence" shall mean the amino acid sequence determined by reading the triplet sequence of nucleotide bases in the cDNA.

As used herein the term "screening a library" shall refer to the process of using a labeled probe to check whether, under the appropriate conditions, there is a sequence complementary to the probe present in a particular DNA library. In addition, "screening a library" could be performed by PCR.

As used herein, the term "PCR" refers to the polymerase chain reaction that is the subject of U.S. Pat. Nos. 4,683,195 and 4,683,202 to Mullis, as well as other improvements now known in the art.

The amino acid described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J Biol. Chem.*, 243:3552–59 (1969), abbreviations for amino acid residues are known in the art.

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bound at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included near the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide", as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementary with the sequence or hybridize therewith and thereby form the template for the synthesis of the extension product.

As used herein, the terms "restriction endonucleases" and "restriction enzymes" refer to enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

The labels most commonly employed for these studies are radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate link.

Proteins can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

A particular assay system developed and utilized in the art is known as a receptor assay. In a receptor assay, the material to be assayed is appropriately labeled and then certain cellular test colonies are inoculated with a quantity of both the label after which binding studies are conducted to determine the extent to which the labeled material binds to the cell receptors. In this way, differences in affinity between materials can be ascertained.

An assay useful in the art is known as a "cis/trans" assay. Briefly, this assay employs two genetic constructs, one of which is typically a plasmid that continually expresses a particular receptor of interest when transfected into an appropriate cell line, and the second of which is a plasmid that expresses a reporter such as luciferase, under the control of a receptor/ligand complex. Thus, for example, if it is desired to evaluate a compound as a ligand for a particular receptor, one of the plasmids would be a construct that results in expression of the receptor in the chosen cell line, while the second plasmid would possess a promoter linked to the luciferase gene in which the response element to the particular receptor is inserted. If the compound under test is an agonist for the receptor, the ligand will complex with the receptor, and the resulting complex will bind the response element and initiate transcription of the luciferase gene. The resulting chemiluminescence is then measured photometrically, and dose response curves are obtained and compared to those of known ligands. The foregoing protocol is described in detail in U.S. Pat. No. 4,981,784.

The current invention is directed to a method of treating neuroectodermal tumors with a neuroectodermal tumorspecific ligand fused to a cytotoxic moiety. Possible neuroectodermal tumor targets include gliomas, meningiomas, ependymonas, medulloblastomas, neuroblastomas, gangliomas, pheochromocytomas, melanomas, PPNET's, small cell carcinoma of the lung, Ewing's sarcoma, and metastatic tumors in the brain. Preferably, the neuroectodermal tumor specific ligand is chlorotoxin fused to a cytotoxic moiety. Examples of possible cytotoxic moieties include gelonin, ricin, saponin, pseudonomas exotoxin, pokeweed antiviral protein, diphtheria toxin, and complement protein.

The current invention is also directed to a neuroectodermal tumor specific therapeutic agent in which the neuroectodermal tumor specific ligand is an antibody against the chlorotoxin receptor believed to be a 72 kDa chloride channel. The antibody may be fused to gelonin, ricin, saponin, pseudonomas exotoxin, pokeweed antiviral protein, diphtheria toxin, or complement proteins.

The current invention is also directed to a method of differentiating neuroectodermal tumor-derived neoplastic tumor tissue from non-neoplastic tissue by incubating the tissue of interest with labeled chlorotoxin and measuring the binding of the labeled chlorotoxin, relative to normal tissue where available. The chlorotoxin may be labeled with either a fluorescent moiety or may be radiolabeled with radiolabels such as $^{131}I$ or $^{125}I$. Fluorescent moieties can be used for detection by fluorescent microscopy or fluorescent activated cell sorting. Radiolabeled chlorotoxin can be detected by positron emission tomography scanning.

The following examples are given for the purpose of illustrating various embodiments of the invention and are not meant to limit the present invention in any fashion.

EXAMPLE 1
Summary of Chlorotoxin Results from Glioma Experiments

Recent studies demonstrated a common antigen is expressed by the vast majority of glioma cells. This antigen is targeted by chlorotoxin (Ctx or TM-601), a 36 amino acid peptide originally isolated from *Leiurus quinquestriatus* scorpion venom. Chlorotoxin selectively binds to the membrane of glioma cells allowing selective targeting of these cells within the CNS (18). The antigen targeted by this peptide appears to be a chloride ion channel although the antigen has not yet been unequivocally identified at the molecular level. Thus far, the data indicates that chlorotoxin binds to a membrane protein of 72 kDa molecular weight that is preferentially expressed in the cytoplasmic membrane of glioma cell. Binding of the peptide enhances glioma cell proliferation (19) and inhibits the ability of glioma cells to migrate in Transwell assays, an in vitro assay to evaluate tumor invasiveness (20). Chlorotoxin appears to exert these effects by reducing the membrane permeability to Cl⁻ ions thereby preventing cell volume changes that are required to allow cells to invade healthy tissue (20). Thus, the most likely action of chlorotoxin is on a glioma chloride channel previously extensively characterized (19).

EXAMPLE 2
Immunohistochemical Staining of Gliomas with Chlorotoxin

Over 250 frozen or paraffin sections of human biopsy tissues were histochemically stained with a chemically synthesized form of chlorotoxin containing a detectable biotin group chemically attached to the N terminus (TM-601). Binding of the TM-601 molecule was observed on selective cells associated with the essentially all glioma tumors with up to 95% positive cells per tumor. Based on these studies, it has been proposed to utilize chlorotoxin as a glioma specific marker and as a potential therapeutic tool for targeting glioma tumors. For such purposes, chlorotoxin linkage of radioactive molecules or cytotoxic moieties such as saporin could be employed.

EXAMPLE 3
Recombinant DNA Manipulation of Chlorotoxin

Using techniques well known in the art, one may prepare recombinant proteins specifically engineered to mimic the binding and action of the native toxin. The biological activity of the synthetic chlorotoxin is as effective for chloride ion channel blockade as the native venom toxin. Recombinant techniques are used to synthesize chlorotoxin in *E coli* using a modified PGEX vector system and the toxin may be linked to various fusion proteins using common restriction sites. After synthesis of recombinant chlorotoxin, it may be linked to various cytotoxic fusion proteins including glutathione-S-transferase (GST), gelonin, ricin, diptheria toxin, complement proteins and radioligands and other such proteins as are well known in the immunotoxin art.

EXAMPLE 4
Antibodies Against the Chlorotoxin-Binding Chloride Ion Channel

Antibodies to the chloride ion channels in glial-derived tumors may be prepared as follows. Polyclonal antisera are generated by injecting fusion proteins created between the glutathione-S-transferase and the chlorotoxin insert into mice or rabbits. Mice are immunized with 0.5 ml of a 1:1 emulsion of 1 mg/ml purified fusion protein in Freund's complete adjuvant and subsequently with two additional injections after 14 and 28 days in Freund's incomplete adjuvant. The mouse and rabbit antibodies are purified from the antisera using the GST fusion protein immobilized on nitrocellulose filters. The antibodies are then examined for binding specificity in various tissues.

EXAMPLE 5
Rationale for the Examination of Neuroectodermally Derived Tumors for Chlorotoxin Binding Given the similarities that can be shared between gliomas and other neuroectodermally-derived cells, and the arguments developed that propose similar propensities of neuroectodermal cells to migrate, a thorough investigation was undertaken to examine neuroectodermally derived tumors for the expression of chlorotoxin binding sites.

EXAMPLE 6
Preparation of Sections from Frozen or Paraffin-Embedded Human Biopsies Most of the samples of human tissuel, from both sexes, all ages and race were obtained through the Cooperative Human Tissue Network, Tissue Procurement at UAB, UAB hospitals and the Human Brain Tissue Bank in London, Canada. Snap frozen tissue and fresh tissue embedded in a freezing gel were sliced at 8 microns and picked up onto positively charged glass slides. The sections were then fixed in 4% paraformaldehyde or milloniqs according to the staining protocol. Paraffin blocks were sectioned and prepared according to standard procedures.

EXAMPLE 7
Examination of Biopsy Samples for Chlorotoxin Binding

Biopsy sections were blocked for 1 hour in 10% normal goat serum in PBS and treated with a dilution of biotinylated chlorotoxin overnight at 4° C. After thorough rinsings, the stainings were developed by avidin-biotin complex (ABC) technique (Vectastain Elite ABC Kit from Vector Laboratories, Burlington, Calif.) and visualized by the colorimetric reaction of DAB (3'3'-diaminobenzidine; Vector Laboratories) with the ABC complex.

The biopsy sections were counterstained with methyl green, a nuclear dye, to more easily visualize the unstained cells. Non-specific background label can vary from experiment to experiment due to changes in the effective concentrations of the label, condition of the tissue or the duration of the reaction. Therefore, a control section was identically stained with methyl green but without the biotinylated chlorotoxin. Positive cell staining is identified by chlorotoxin-labeling above background when compared to its individual control of a successive slice. Cells containing high amounts of endogenous peroxidase exhibit dark background staining in the controls due to the reaction of DAB with the peroxidases.

Finally, a third adjacent section was stained with both hematoxylin, a cell nuclei specific stain, and eosin, a cytoplasmic stain. Therefore, for each tissue analyzed, three adjacent section were stained. These are shown in photomicrographs providing evidence of the specificity of TM-601 chlorotoxin binding to tumors of neuroectodermal derivation in comparison to controls. In the photomicrographs, adjacent sections are identified as follows: TM-601: biotinylated chlorotoxin detected by a brown reaction product of DAB with the biotin and further counterstained with methyl green; Control: the control section stained with only methyl green; and, H&E: the hematoxylin and eosin stained section.

EXAMPLE 8
Glioblastoma Multiforme (GBM) Tumors

Figure 2:
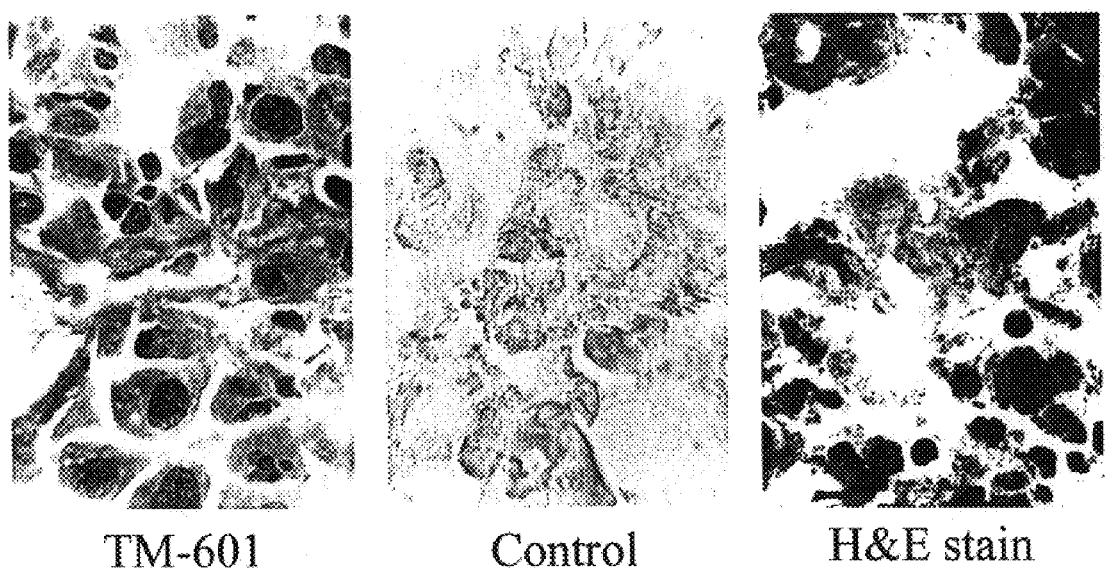
FIG. 2 demonstrates that normal brain is not immunohistochemically stained by biotinylated chlorotoxin. TM-601: biotinylated chlorotoxin, counter-stained with methyl green; Control: methyl green only; and, H&E stain: hematoxylin and eosin. Normal brain was also stained with biotinylated antibodies against GFAP (Glial Fibrillary Acidic Protein) which positively stains astrocytes in normal brain tissue.

Glioblastoma multiforme (GBM) were stained with the biotinylated chlorotoxin (TM-601). These tumors are extremely reactive to biotinylated chlorotoxin as 25 out of 25 patient samples tested positive as seen in FIG. 1. This glioblastoma multiforme can be compared to the staining of the normal human brain tissue with biotinylated chlorotoxin (18/23 negative). FIG. 2 shows a representative staining. Normal brain tissue demonstrates a lack of TM-601 staining. This is consistent with earlier evidence of specificity of chlorotoxin binding to gliomas.

EXAMPLE 9
GFAP Staining in the Normal Brain Tissue

The biopsy section was blocked for 1 hour in 10% normal goat serum in PBS and then stained with antibodies against glial fibrillary acidic protein (GFAP; DAKO corporation, Carpinteria Calif.) overnight. The secondary antibody conjuaged to peroxidase was applied to the rinsed tissue for 2 hours, rinsed again before the stain was visualized with DAB. A typical glial fibrillary acidic protein stain of normal brain is shown in FIG. 2. Normal brain was positive for glial fibrillary acidic protein staining where it stained the astrocytes typically present in normal tissue.

EXAMPLE 10
Neuroblastomas

Figure 3:
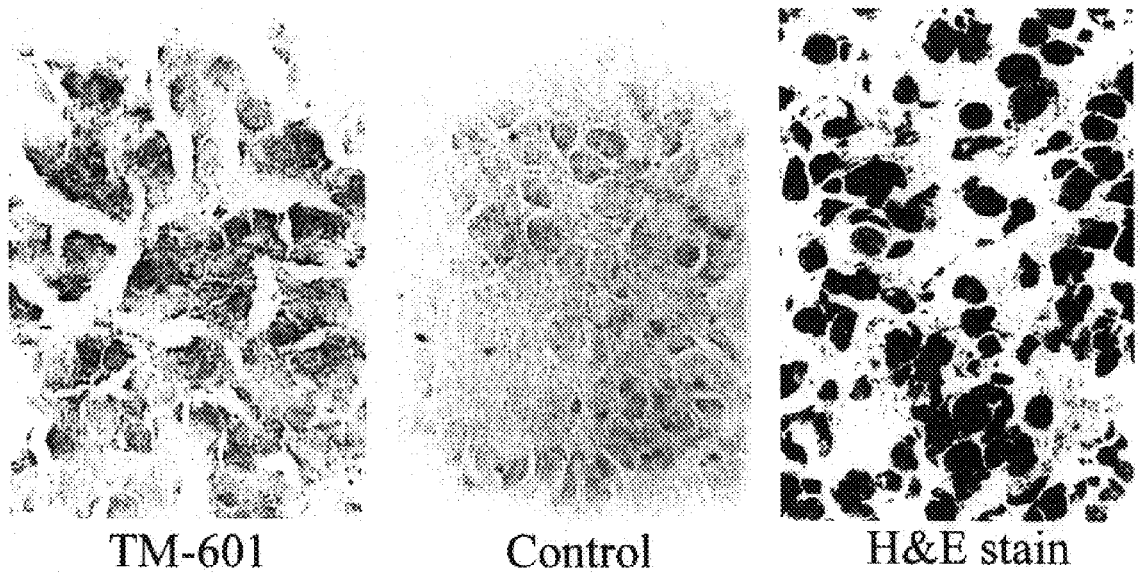
FIG. 3 shows chlorotoxin staining of an adrenal mass neuroblastoma tumor. TM-601: biotinylated chlorotoxin, counter-stained with methyl green; Control: methyl green only; and, H&E stain: hematoxylin and eosin.

Neuroblastomas are a tumor primarily found in children with a high incidence in the adrenals. Neuroblastoma show TM-601 reactivity above the control staining as seen in FIG. 3. Six out of seven neuroblastomas were positive for chlorotoxin binding.

EXAMPLE 11
Pheochromocytomas

Figure 4:
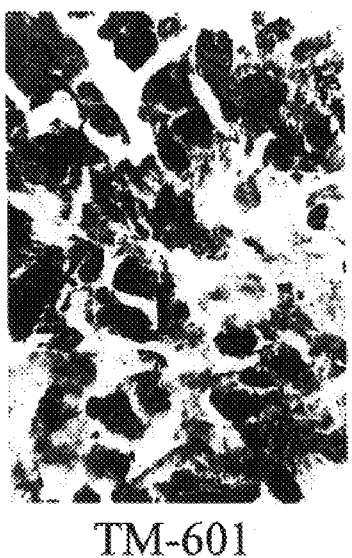
FIG. 4 illustrates that biotinylated chlorotoxin immunohistochemically stains pheochromocytomas. TM-601: biotinylated chlorotoxin, counter-stained with methyl green; Control: methyl green only; and, H&E stain: hematoxylin and eosin.
Figure 4:
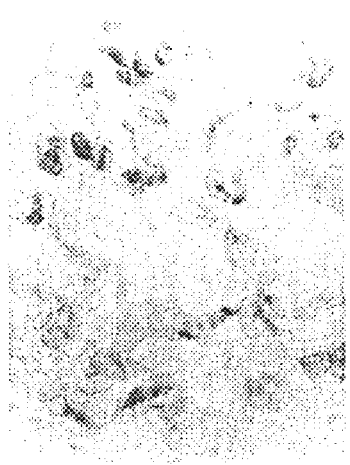
Figure 4:
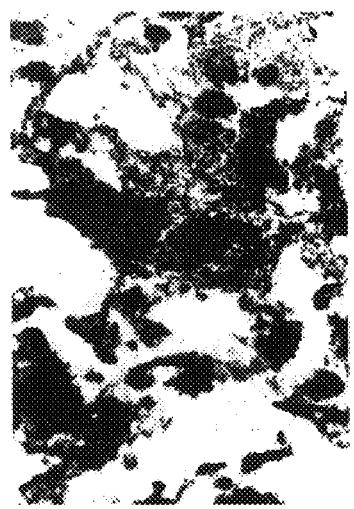
Figure 5:
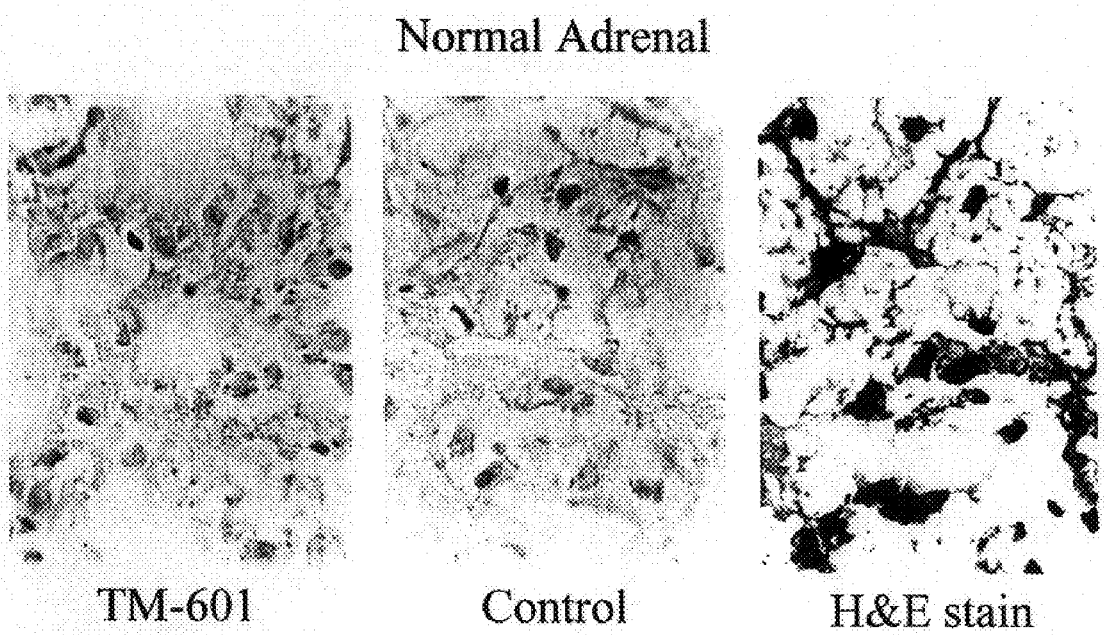
FIG. 5 illustrates that normal adrenal tissue is not immunohistochemically stained by biotinylated chlorotoxin. TM-601: biotinylated chlorotoxin, counter-stained with methyl green; Control: methyl green only; and, H&E stain: hematoxylin and eosin.

Pheochromocytomas are neoplastic chromaffin cells of the adrenal glands. This tumor also show a high degree of staining as seen in FIG. 4. Five out of six pheochromocytomas were positive for staining with biotinylated chlorotoxin, especially in comparison to TM-601 staining of the normal adrenals (3/3 negative) seen in FIG. 5.

EXAMPLE 12

Melanomas

Figure 6:
FIG. 6 shows the immunohistochemical staining with biotinylated chlorotoxin of melanoma tumor cells metastasized to the brain TM-601: biotinylated chlorotoxin, counter-stained with methyl green; Control: methyl green only; and, H&E stain: hematoxylin and eosin.
Figure 6:
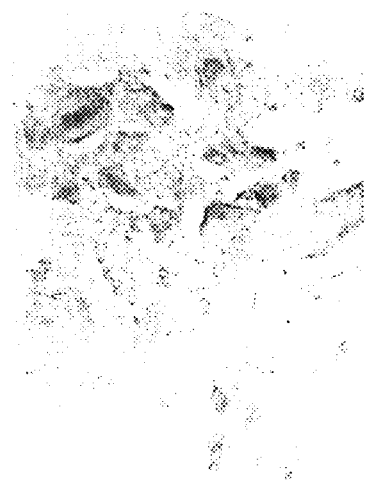
Figure 6:
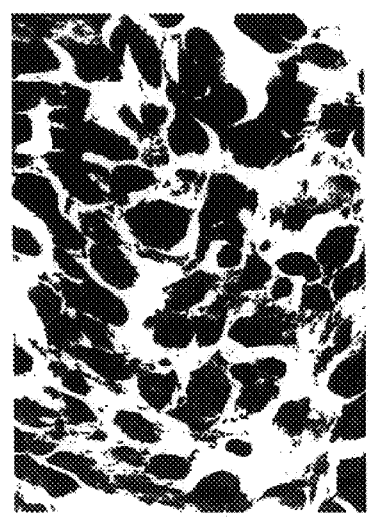
Figure 7:
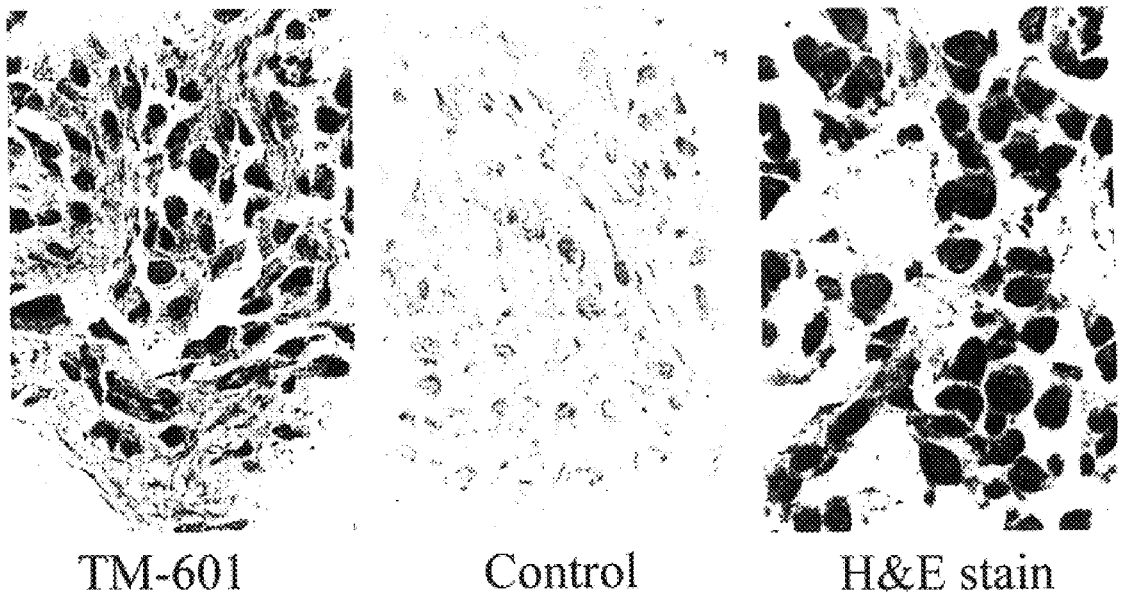
FIG. 7 illustrates biotinylated chlorotoxin immunohistochemical staining of melanoma tumor cells metastasized to the lung. TM-601: biotinylated chlorotoxin, counter-stained with methyl green; Control: methyl green only; and, H&E stain: hematoxylin and eosin.
Figure 8:
FIG. 8 shows immunohistochemical staining of normal skin with biotinylated chlorotoxin. TM-601: biotinylated chlorotoxin, counter-stained with methyl green; Control: methyl green only; and, H&E stain: hematoxylin and eosin.
Figure 8:
Figure 8:
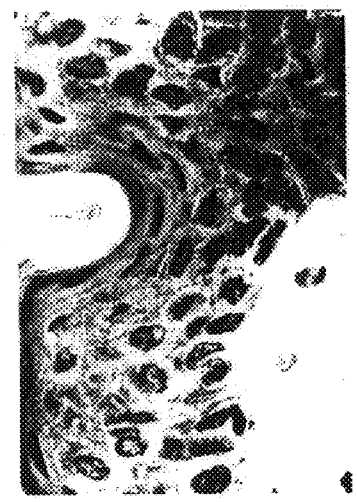

FIG. 6 shows the biotinylated chlorotoxin staining of a melanoma metastasized to the brain. Seven out of seven melanoma brain metastasis were positive for TM-601. In addition, melanoma metastasized to the lung were analyzed as seen in FIG. 7. Normal skin, however, is unreactive to TM-601 (6/6 negative) (FIG. 8) although there is some background staining in the melanocytes even in the controls.

EXAMPLE 13

Small Cell Lung Carcinomas

Figure 9:
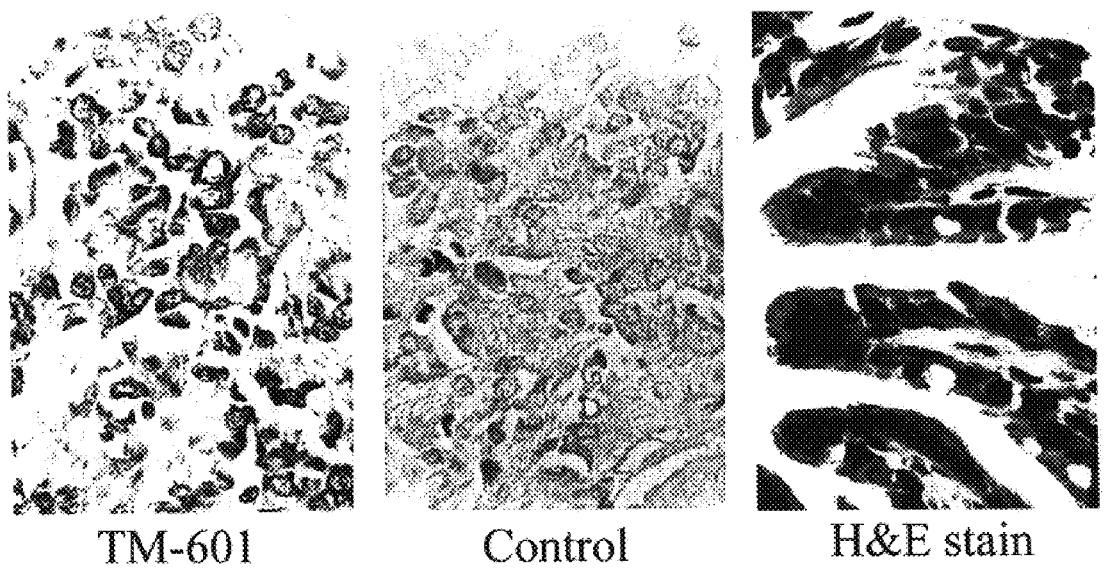
FIG. 9 shows immunohistochemical staining of small cell lung carcinomas with biotinylated chlorotoxin. TM-601: biotinylated chlorotoxin, counter-stained with methyl green; Control: methyl green only; and, H&E stain: hematoxylin and eosin.
Figure 10:
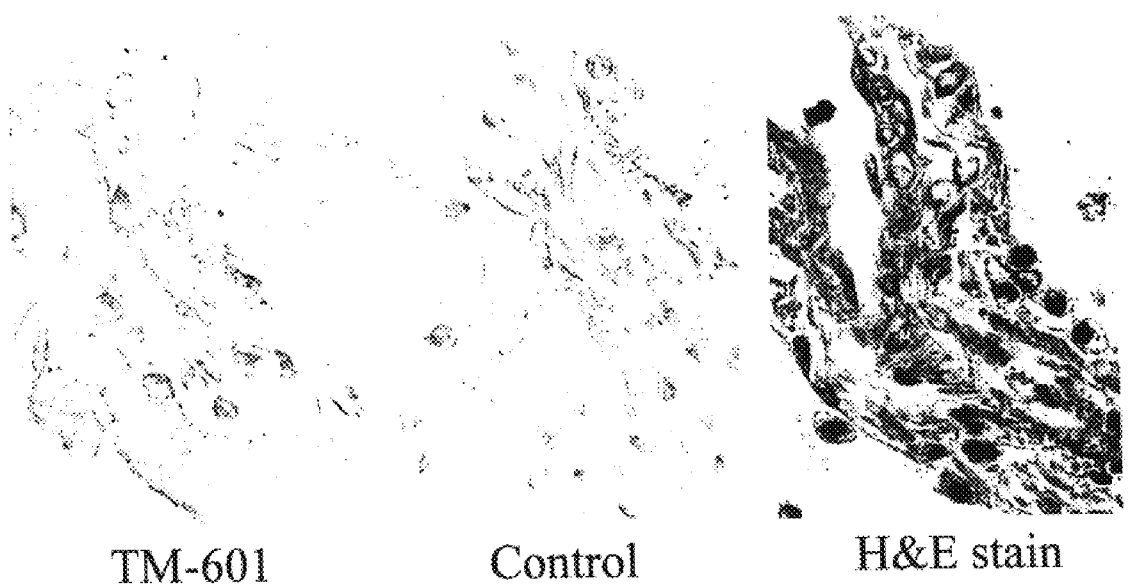
FIG. 10 shows that biotinylated chlorotoxin does not immunohistochemically stain normal lung tissue. TM-601: biotinylated chlorotoxin, counter-stained with methyl green; Control: methyl green only; and, H&E stain: hematoxylin and eosin.

Small cell lung carcinomas are reactive to TM-601. There is good contrast between the cells that stain and those that do not (FIG. 9). The cells positive for TM-601 in the control (middle panel) are red blood cells which present high levels of background peroxidase stain. This TM-601 specificity can be further demonstrated by comparing the TM-601 staining of the small cell carcinoma (2/3 positive) and the normal lung (3/3 negative) (FIG. 10).

EXAMPLE 14

Medulloblastomas

Figure 11:
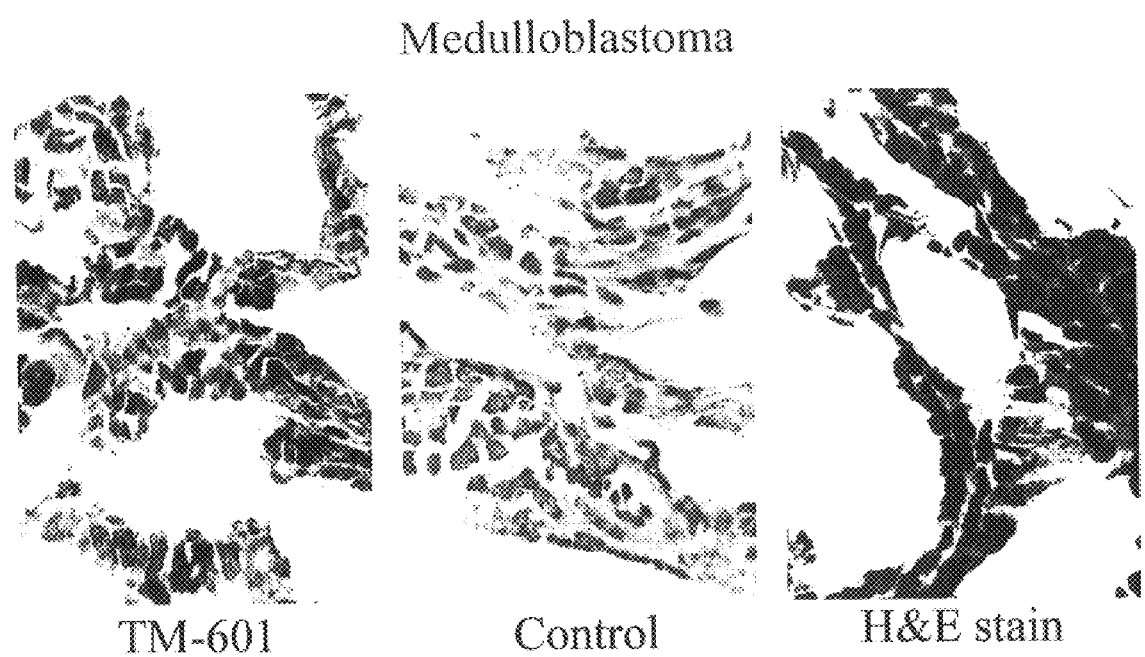
FIG. 11 shows the immunohistochemical staining of a medulloblastoma tumor with biotinylated chlorotoxin. TM-601: biotinylated chlorotoxin, counter-stained with methyl green; Control: methyl green only; and, H&E stain: hematoxylin and eosin.

Another neuroectodermally derived tumor type are the medulloblastomas. They exhibit specific reactivity to TM-601 as seen in FIG. 11 (4/4 positive).

EXAMPLE 15

Ewing's Sarcoma

Figure 12:
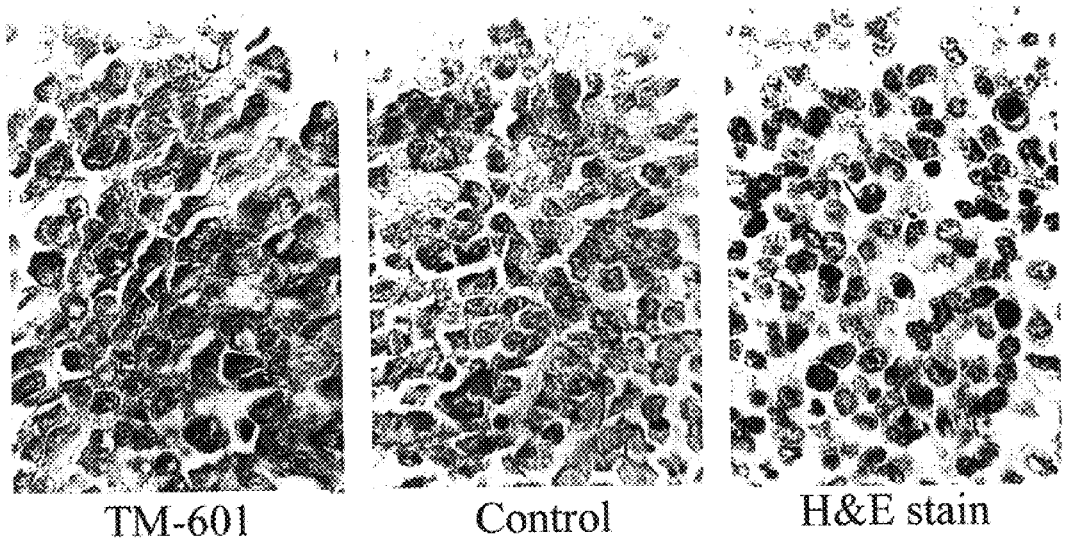
FIG. 12 shows that the rare, neuroectodermally derived bone cancer, Ewing's sarcoma, also exhibits positive immunohistochemical staining with biotinylated chlorotoxin. TM-601: biotinylated chlorotoxin, counter-stained with methyl green; Control: methyl green only; and, H&E stain: hematoxylin and eosin.

Ewing's sarcoma, a rare bone cancer sometimes found in soft tissue, is TM-601 positive (2/2) (FIG. 12).

EXAMPLE 16

Testing of Potential Sites of Chlorotoxin Administration for Side Effects

Figure 13:
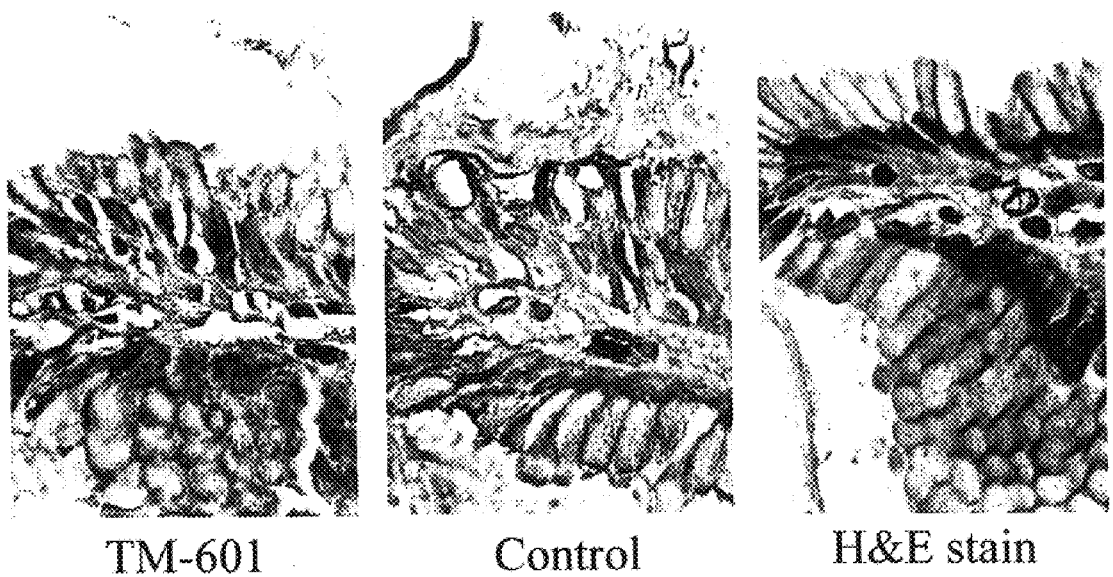
FIG. 13 shows the negative results obtained in the immunohistochemical staining of normal stomach tissue with biotinylated chlorotoxin. TM-601: biotinylated chlorotoxin, counter-stained with methyl green; Control: methyl green only; and, H&E stain: hematoxylin and eosin.
Figure 14:
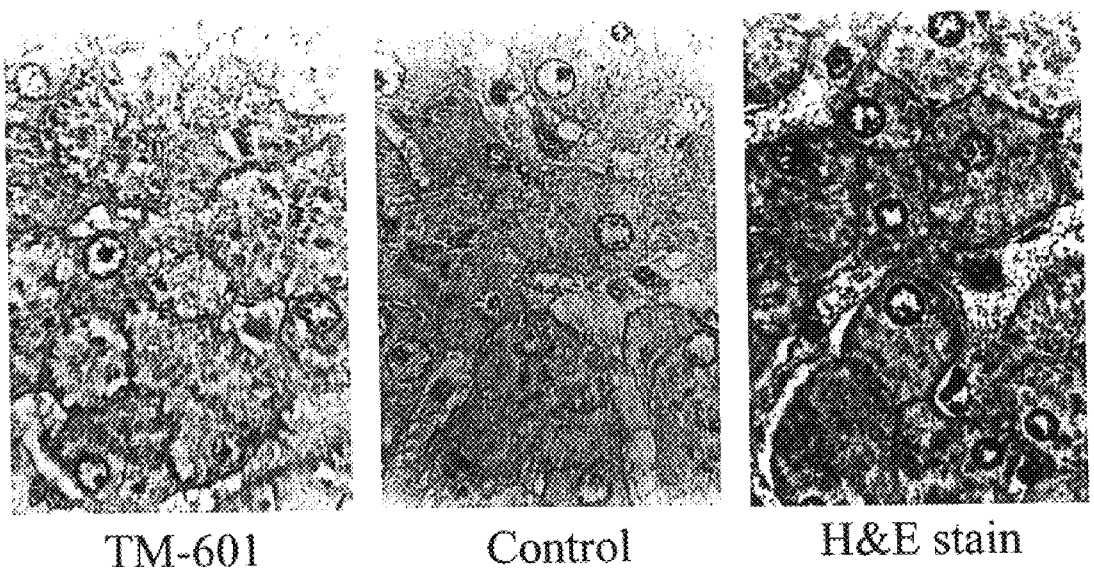
FIG. 14 shows the lack of immunohistochemical staining of normal liver tissue with biotinylated chlorotoxin. TM-601: biotinylated chlorotoxin, counter-stained with methyl green; Control: methyl green only; and, H&E stain: hematoxylin and eosin.
Figure 15:
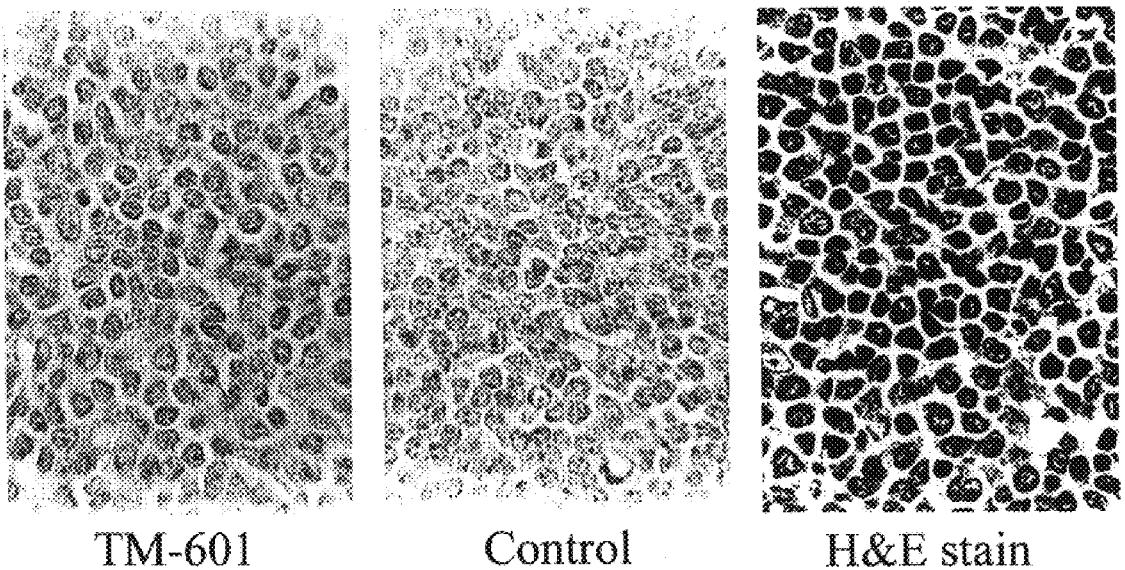
FIG. 15 demonstrates that normal spleen tissue is not immunohistochemically stained by with biotinylated chlorotoxin. TM-601: biotinylated chlorotoxin, counter-stained with methyl green; Control: methyl green only; and, H&E stain: hematoxylin and eosin.

To aid in the design of drug therapy with this product, various normal tissues were stained with TM-601 to determine possible sites where side effects may occur. Preliminary evidence indicates that some of the most common targets for side effects such as the stomach and liver, are TM-601 negative (2/2 negative samples for both tissues, thus far) (FIGS. 13 and 14 respectively). The staining of spleen tissue is also shown in FIG. 15 (3/3 negative). The TM-601 staining of other normal human tissues is summarized in Table 1.

TABLE I

| Tumor or Tissue Type | # of Cases | Chlorotoxin-binding |
|---|---|---|
| Primary Brain Tumors: Gliomas: | | |
| WHO grade IV: glioblastoma multiforme | 25 | Positive |
| WHO grade III: anaplastic astrocytoma | 2 | Positive |
| WHO grade II: low grade | 2 | Positive |
| WHO grade I: pliocytic astrocytoma | 11 | Positive |
| Oligodendrogliomas | 6 | Positive |
| Other gliomas | 3 | Positive |
| Gangliomas | 3 | Positive |
| Meningiomas | 18 | Positive |
| Ependymomas | 3 | Positive |

TABLE I-continued

| Tumor or Tissue Type | # of Cases | Chlorotoxin-binding |
|---|---|---|
| Other Primary Brain Tumors: | | |
| Epidermoid cysts in brain | 3 | 2/3 Positive |
| Brain tumors-unknown pathology | 15 | 14/15 Positive |
| Pituitary gland of GBM patient | 2 | Positive |
| Secondary Brain Tumors: | | |
| Metastatic tumors to brain | 14 | 12/14 Positive |
| Comparison of Brain Tissues | | |
| Alzheimer brains | 8 | Negative |
| Brain, normal or uninvolved | 24 | 18/24 Negative |
| Epilepsy/gliosis/stroke | 6 | Positive |
| Uninvolved brain of GBM | 3 | Negative (autopsy) |
| Tumors of Neuro Ectodermal Origin: | | |
| Medulloblastoma | 4 | Positive |
| Neuroblastoma | 7 | 6/7 Positive |
| Ganglioneuroma | 4 | Positive |
| Melanomas | 7 | Positive |
| Pheochromocytoma | 6 | 5/6 Positive |
| PPNET | 1 | Negative |
| Small cell carcinoma lung | 3 | 2/3 Positive |
| Ewing's sarcoma | 2 | Positive |
| Other Human Tissues | | |
| Colon | 3 | Negative |
| Endometrium/myometrium | 2 | Negative |
| Heart | 2 | Negative |
| Kidney | 2 | Cortex is Positive/ Medulla is Negative |
| Adrenal Gland | 3 | Negative |
| Liver | 3 | Negative |
| Lung | 3 | Negative |
| Lung, small cell carcinoma | 1 | Positive |
| Meninges | 3 | Negative |
| Muscle, skeletal | 2 | Negative |
| Pancreas, fibrosis | 1 | Negative |
| Ovary | 2 | Mostly Negative/a few cells are positive |
| Skin, from thigh, abdomen or breast | 6 | Negative |
| Spleen | 3 | Negative |
| Stomach | 2 | Negative |
| Testes | 2 | Mostly negative/a few cells are positive |
| Thyroid | 1 | Negative |

EXAMPLE 17

Summary of Tested Tumors and Tissues

As summarized in Table 1, the vast majority of neuroectodermally derived tumors bind chlorotoxin, indicating that chlorotoxin has a more widespread utility to target tumors of neuroectodermal origin. Specifically, primitive neuroectodermal tumor tumors have been tested from 34 patients, 31 of which showed chlorotoxin specificity in the tumor material as seen in Table 1. This staining was compared with the chlorotoxin staining of other types of CNS and PNS tumors as well as the comparison to various normal human tissues.

TM-601 specifically associates with neuroectodermally-derived tumors including medulloblastomas, neuroblastomas, ganglioneuromas, melanomas, pheochromocytomas, small cell lung carcinomas and Ewing's sarcomas. Thus, chlorotoxin-derived molecules can be utilized to target specifically for therapeutic or diagnostic purposes the above identified neuroectodermally-derived tumors. Likewise, these tumors can also be targeted by other molecules such as antibodies that bind to the chlorotoxin receptor, presumed to be the 72 kD Cl⁻ ion channel.

The following references were cited herein:
1. Hemizygous or homozygous deletion of the chromosomal region containing the p16INK4a gene is associated with 1. amplification of the EGF receptor gene in glioblastomas. Hegi M E, Hausen A Z, Ruedi D, Malin G and Kleihues P. (1997) Int. J. Cancer 73:57–63.
2. Ras activation in astrocytomas and neurofibromas. Guha A. (1998) Can J. Neurol. Sci. 25:267–281.
3. Tumor antigens in astrocytic gliomas. Kurpad S N, Zhao X G, Wikstrand C J, Batra S K, McLendon R E, and Bigner D D. (1995) Glia 15:244–256.
4. Iodine-131-labeled anti-tenascin monoclonal antibody 81C6 treatment of patients with recurrent malignant gliomas: phase 1 trial results. Bigner D D, Brown M T, Friedman A H, Coleman R E, Akabani G, Friedman H S, Thorstad W L, McLendon R E, Bigner S H, Zhao X-G, Pegram C N, Wikstrand C J, Herndon J E, Vick N A, Paleologos N, Cokgor I, Provenzale J M and Zalutsky M R. (1998) J. Clin. Onco. 16:2202–2212.
5. Trilateral tumors in four different lines of transgenic mice expressing SV40 T-antigen. (1996) Marcus D M, Lasudry J G, Windle J, Howes K A, al Ubaidi M R, Baehr W, Overbeek P

FEDERAL FUNDING LEGEND

This invention was produced in part using funds from the Federal government under NIH grant no. R01 NS 36692. Accordingly, the Federal government has certain rights in this invention. A, Font R L, and Albert D M. Invest. Ophthalmol. Vis Sci 37:392–396.
6. Molecular detection of tumor-associated antigens shared by human cutaneous melanomas and gliomas. Chi D D J, Merchant R E, Rand R, Conrad A J, Garrison D, Turner R, Morton D L, and Hoon D S B. (1997) Am. J. Pathol. 150:2143–2152.
7. Pathology and Genetics of Tumors of the Nervous System. Eds. Paul Kleihues and Webster K. Cavenee, International Agency for Research on Cancer, Lyon, 1997.
8. Peripheral primitive neuroectodermal tumor of the ovary confirmed by CD99 immunostaining, karyotypic analysis, and RT-PCR for EWS/FLI-1 chimeric mRNA. Kawauchi S, Fukuda T, Miyamoto S, Yoshioka J, Shirahama S, Saito T, and Sukamoto N. (1998) Am J Surg. Pathol. 11:1417–1422.
9. Cytology of typical and atypical Ewing's sarcoma/PNET. Renshaw A A, Perez-Atayde A R, Gletcher J A, and Granter S R. (1996) Am J. Clin Pathol 106:620–624.
10. C-kit is expressed in soft tissue sarcoma of neuroectodermic origin and its ligand prevents apoptosis of neoplastic cells. Ricotti E, Fagioli F, Garelli E, Linari C, Crescenzio N, Horenstein A L, Pistamiglio P, Vai S, Berger M, Cordero di Montezemolo L, Madon E, and Basso G. (1998) Blood 91:2397–2405.
11. Interleukin-1 alpha, IL-1 beta, IL-1R type1, IL-1 R antagonist, and TGF-beta 1 mRNAs in pediatric astrocytomas, ependymomas, and primitive neuroectodermal tumors. Ilyin S E, Gonzalez-Gomez I, Gilles F H, and Plata-Salaman C R. (1998) Mol. Chem. Neuropathol. 33:125–137.
12. Immunohistochemical characterization of primitive neuroectodermal tumors and their possible relationship to the stepwise ontogenetic development of the CNS. 2. Tumor studies. Kleinert R. (1991) Acta Neuropathol 82:508–15.
13. Proteins of the intermediate filament cytoskeleton as markers for astrocytes and human astrocytomas. Yang H Y, Lieska N, Shao D, Kriho V, and Pappas G D. (1994) Mol.Chem. Neuropathol 21:155–176.
14. Human primitive neuroectodermal tumour cells behave as multipotent neural precursors in response to FGF2. Derrington E A, Dufay N, Rudkin B B, and Belin M-F. (1998) Oncogene 17:1663–1672.
15. Neuroectodermal tumors of the peripheral and the central nervous system share neuroendocrine N-CAM-related antigens with small cell lung carcinomas. Molenaar W M, de Leij L, and Trojanowski J Q. (1991) Acta Neuropathol. 83:46–54.
16. Neurotrophins and neuronal versus glial differentiation in medulloblastomas and other pediatric brain tumors. Tajima Y, Molina R P Jr, Rorke L B, Kaplan D R, Radeke M, Feinstein S C, Lee V M, and Trojanowski J Q. (1998) Acta Neuropathol. 95:325–332.
17. Expression of c-src in cultured human neuroblastoma and small-cell lung carcinoma cell lines correlates with neurocrine differentiation. Mellstrom K, Bjelfman C, Hammerling U, and Pahlam S. (1987) Mol Cell Biol 7:4178–4184.
18. Use of chlorotoxin for targeting of primary brain tumors. Soroceanu L, Gillespie Y, Khazaeli M B and Sontheimer H W. (1998) Cancer Res. 58:4871–4879.
19. Cell cycle-dependent expression of a glioma-specific chloride current: proposed link to cytoskeletal changes. Ullrich N and Sontheimer H. (1997) Am J. Physiol. 273:C1290–1297.
20. Modulation of glioma cell migration and invasion using Cl– and K+ ion channel blockers Soroceanu L, Manning T J Jr., and Sontheimer H. (1999) J. Neuroscience. Submitted.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of detecting a neuroectodermal tumor in a patient comprising:
   (a) adding chlorotoxin to a patient tissue sample; and
   (b) detecting the binding of chlorotoxin to the tissue sample wherein an elevated level of binding relative to normal tissue is indicative of the presence of the neuroectodermal tumor.

2. The method of claim 1 wherein the neuroectodermal tumor is selected from the group consisting of glioma, meningioma, ependymonas, medulloblastoma, neuroblastoma, glioblastoma, ganglioma, pheochromocytoma, melanoma, Ewing's sarcoma, small cell lung carcinoma and metastatic brain tumors.

3. The method of claim 1 wherein the chlorotoxin is labeled.

4. The method of claim 3 wherein the chlorotoxin label is detected by enzyme-linked immunosorbent assay.

5. The method of claim 3 wherein the chlorotoxin label is a radiolabel.

6. The method of claim 5 wherein the radiolabel is selected from the group consisting of $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{186}Re$, $^{131}I$ and $^{125}I$.

7. The method of any one of claims 5 or 6 wherein the radiolabel is detected by positron emission tomography scanning.

8. The method of claim 3 wherein the chlorotoxin label is a fluorescent moiety.

9. The method of claim 8 wherein the fluorescent moiety is selected from the group consisting of fluorescein, rhodamine, auramine, Texas Red, AMCA blue and Lucifer Yellow.

10. The method according to claim 8 wherein the fluorescent moiety is detected by a method selected from the group consisting of fluorescent microscopy and fluorescent activated cell sorting.

11. The method of claim 3 wherein the chlorotoxin label is biotin.

12. The method of claim 11 further comprising the step of contacting the sample with avidin to form avidin-biotin-labeled chlorotoxin complexes.

13. The method of claim 12 further comprising the step of contacting the avidin-biotin-labeled chlorotoxin complexes with 3'3'-diaminobenzidine to form a colormetric product wherein the level of the colormetric product is indicative of the level of chlorotoxin binding.

14. The method of claim 3 wherein the detecting of the binding of chlorotoxin to the tissue sample comprises measuring the binding of chlorotoxin to the tissue sample.

15. The method of claim 1 wherein the tissue sample is frozen.

16. The method of claim 1 wherein the tissue sample is embedded in paraffin.

17. The method of any one of claims 15 or 16 wherein the tissue sample is counterstained.

18. The method of claim 17 wherein the counterstain is selected from the group consisting of methyl green, hematoxylin and eosin.

* * * * *